United States Patent [19]

Guex et al.

[11] 4,295,517

[45] Oct. 20, 1981

[54] REUSABLE HEAT DEVICES CONTAINING XYLITOL AS THE HEAT-STORAGE MATERIAL

[76] Inventors: Woldemar Guex, 4 Spechtweg, Bottmingen; Heinrich Klaeui, 77 Kilchgrundstrasse, Riehen; Horst Pauling, 39 Ruchholzstrasse, Bottmingen; Felix Voirol, 26 Poolstrasse, Füllinsdorf, all of Switzerland

[21] Appl. No.: 152,056

[22] Filed: May 20, 1980

Related U.S. Application Data

[62] Division of Ser. No. 916,424, Jun. 16, 1978, abandoned.

[51] Int. Cl.³ .............................................. F28D 21/00
[52] U.S. Cl. ....................................... 165/1; 126/263; 252/70; 165/104.17
[58] Field of Search ...................... 165/104 S; 252/70; 126/263

[56] References Cited

U.S. PATENT DOCUMENTS

| 3,463,161 | 8/1969 | Andrassy | 252/70 X |
| 3,899,593 | 8/1975 | Hammond et al. | 426/3 |
| 3,960,205 | 6/1976 | Laing | 126/400 X |
| 4,199,021 | 4/1980 | Thoma | 252/70 X |

FOREIGN PATENT DOCUMENTS 50-90989  2/1975  Japan ..................................... 252/70

*Primary Examiner*—Albert W. Davis
*Attorney, Agent, or Firm*—Jon S. Saxe; George M. Gould; William M. Farley

[57] ABSTRACT

Both heat devices containing a supercooled xylitol and the use of supercooled xylitol as a heat source are disclosed.

6 Claims, No Drawings

REUSABLE HEAT DEVICES CONTAINING XYLITOL AS THE HEAT-STORAGE MATERIAL

This is a division of application Ser. No. 916,424 filed June 16, 1978 now abandoned.

BACKGROUND OF THE INVENTION

This invention relates to reusable heat sources, and to methods for their use, which devices contain a supercooled material, either as a melt or in a solution, which, when crystallized, liberates heat.

Many types of heat devices are known which employ a supercooled melt or aqueous salt solution. These heat devices are stored with the heat source maintained as a supercooled melt or solution. When needed, the devices can be activated by crystallization of the melt or the salt in solution with the resulting release of heat.

An example of such a heat device and a method for its use is disclosed in U.S. Pat. No. 4,077,390. Therein a heat pack containing a supercooled aqueous sodium acetate solution is used as the heat source. Activation, i.e. crystallization, is accomplished using a flexible metal strip contained in the heat pack. Crystallization of the sodium acetate results in the liberation of heat.

DETAILED DESCRIPTION OF THE INVENTION

This invention relates to the use of xylitol as a heat source in heat devices.

Xylitol is a polyhydric alcohol prepared by the hydrolysis of xylan to xylose followed by the reduction of the xylose to xylitol.

Xylitol has a very high negative heat of crystallization—61.61 kcal/kg. Its crystallization, therefore, results in the evolution of a considerable quantity of heat.

This invention is, thus, directed to a process utilizing xylitol with its high heat of crystallization, as a heat-storage material.

The instant invention is also based on the discovery that xylitol, in addition to its high heat of crystallization, forms a distinct metastable melt. Thus, a xylitol melt can be cooled to temperatures, e.g. room temperature, which are well below its melting point (93°–94.5° C.). The xylitol remains in the form of a stable, supercooled melt which does not crystallize spontaneously.

In addition, the resulting supercooled xylitol melt or xylitol solution is suitably stable so that it does not crystallize unintentionally, e.g. by shaking, etc.

Further, the xylitol melt or solution should be maintained in a closed container to prevent the spontaneous crystallization by foreign bodies as, for example, dust.

Under the influence of a stimulus, xylitol crystallization is initialed and there is a consequent release of the heat of crystallization. This cycle is repeatable, i.e., the xylitol is remelted by heating to a temperature above its melting point, followed by cooling to below its melting point and storage until needed.

Thus, xylitol offers, in its combination of a high heat of crystallization and a melting point just below the boiling point of water, significant advantages as a heat-storage material in reusable heat devices.

In the devices and methods of this invention, xylitol can be used not only as a melt but also in a liquid as, for example, a super-saturated aqueous solution, a propylene glycol solution and the like.

In the procedure of this invention xylitol is melted in a container, preferably closed, and then allowed to cool to a temperature below the melting point of xylitol. Cooling, preferably to room temperature, is carried out under conditions such that crystallization does not occur. Crystallization is effected, when desired to achieve a heating effect, by using any known crystallization method as, for example, by seeding with xylitol crystals, scratching the container walls or by the use of ultrasonics.

The xylitol for use in the methods of this invention can be contained in a gas-tight container as, for example, a plastic bag. Suitable plastic material include polyvinyl chloride, polyethylene, nylon and the like. Many other materials, including metal, would be suitable for use as containers. The main criterion, of course, is that the materials be heat conductive.

Reusable heat devices containing xylitol as the heat-storage material have many possible applications.

For example, as noted above, a supercooled xylitol in a gas-tight, flexible plastic bag can be crystallized when needed by kneading the bag. Further, crystallization can be achieved in such bags by placing a smaller bag containing a film having adhered thereon xylitol crystals. Kneading will break the smaller bag and, thus, release the xylitol crystals into the melt.

Such packaged heat devices can be used, for example, as heat protectors for sensitive plants in emergency situations, and for thawing frozen pipes and apparatus especially where other means, such as the use of an open flame, are prohibited for safety reasons.

These devices can also be used for heating food containers as, for example, in airplanes. One of the most important applications of the method of this invention is in a system for heating rooms. The heat devices containing xylitol or a saturated xylitol solution would line the walls, floor or ceiling of the room to be heated. The energy required for melting of the xylitol in the devices could be supplied by any usual method such as electric heaters inserted in the devices or solar energy means and the like.

In such a room heating system, the container for the xylitol could be in heat-conducting contact with another container to which the quantity of heat liberated upon crystallization of the xylitol is transferred. Such second container could be filled with, e.g., water or other liquid which would be, in turn, heated.

Crystallization of the xylitol in such a system could be achieved, for example, by an ultrasonic source.

To insure a continuous release of heat, a serial arrangement of heat devices containing xylitol can be used. Thus, by means of a control mechanism, certain systems would be charged (i.e., heated above the xylitol melting point) while other systems would be crystallizing and releasing heat.

The following Example illustrates the invention.

EXAMPLE 1

200 kg. of xylitol are heated to 94° C. in a closed container. The container can also have heating elements and/or heat exchangers (for solar collectors). The resulting stable xylitol melt is then cooled to room temperature.

To initiate crystallization, powdered xylitol is added to the melt. Upon crystallization, a considerable quantity of heat is evolved, i.e., about 8000 kcal.

After crystallization and dissipation of the heat evolved, the xylitol can be reheated to above its melting point and the cycle started again.

While this Example illustrates crystallization of xylitol by seeding, the preferred methods for initiating crystallization are by the use of ultrasonics or by the use of mechanical means to scratch the interior surface of the closed container system.

We claim:

1. A method for providing a source of heat which comprises
   (a) adding, as a heat storage material, xylitol to a container;
   (b) heating the xylitol in the container to a temperature above its melting point;
   (c) cooling the resulting melt to a temperature below the melting point of xylitol without crystallizing the xylitol and
   (d) initiating crystallization of the xylitol
   whereby the release of the heat of crystallization of xylitol provides a source of heat.

2. The method of claim 1 wherein the xylitol is present as a powder.

3. The method of claim 1 wherein the xylitol is present as a super-saturated solution.

4. The method of claim 1 wherein crystallization is effected by seeding the cooled melt with xylitol crystals.

5. The method of claim 1 wherein crystallization is effected by ultrasonic techniques.

6. The method of claim 1 wherein crystallization is effected by mechanical techniques.

* * * * *